US012000182B2

United States Patent
Spick et al.

(10) Patent No.: US 12,000,182 B2
(45) Date of Patent: Jun. 4, 2024

(54) DEVICE FOR DETECTING INTENTION TO LOCK OR UNLOCK A MOTOR VEHICLE DOOR AND ASSOCIATED METHOD

(71) Applicant: VITESCO TECHNOLOGIES GMBH, Hanover (DE)

(72) Inventors: Gabriel Spick, Toulouse (FR); Mathieu Girodin, Toulouse (FR); Steffen Eckhardt, Toulouse (FR)

(73) Assignee: VITESCO TECHNOLOGIES GMBH, Hanover (DE)

( * ) Notice: Subject to any disclaimer, the term of this patent is extended or adjusted under 35 U.S.C. 154(b) by 510 days.

(21) Appl. No.: 17/286,143

(22) PCT Filed: Oct. 15, 2019

(86) PCT No.: PCT/EP2019/077859
§ 371 (c)(1),
(2) Date: Apr. 16, 2021

(87) PCT Pub. No.: WO2020/078944
PCT Pub. Date: Apr. 23, 2020

(65) Prior Publication Data
US 2021/0355718 A1 Nov. 18, 2021

(30) Foreign Application Priority Data
Oct. 19, 2018 (FR) ...................................... 1859691

(51) Int. Cl.
*E05B 81/76* (2014.01)
*B60R 25/31* (2013.01)
(Continued)

(52) U.S. Cl.
CPC .............. *E05B 81/77* (2013.01); *B60R 25/31* (2013.01); *E05B 81/78* (2013.01); *G01R 27/02* (2013.01);
(Continued)

(58) Field of Classification Search
CPC .......... E05B 81/77; E05B 81/78; E05B 77/34; B60R 25/31; G01V 3/38; G07C 9/00944;
(Continued)

(56) References Cited

U.S. PATENT DOCUMENTS 8,125,456 B2  2/2012  Krah et al.
8,382,170 B2  2/2013  Ieda et al.
(Continued)

FOREIGN PATENT DOCUMENTS

CN  101432036 A  5/2009
CN  201315054 Y  9/2009
(Continued)

OTHER PUBLICATIONS

Notice of Allowance issued in Chinese Patent Application No. 201980068530.0 dated Nov. 22, 2022.
(Continued)

*Primary Examiner* — Raul J Rios Russo
(74) *Attorney, Agent, or Firm* — NIXON & VANDERHYE

(57) ABSTRACT

Disclosed is a device detecting intention to lock or unlock a vehicle door, including: a first capacitive sensor including a first electrode, detecting the approach and/or contact of a human body part in a predetermined region around the handle; a first sensor controller, generating a first approach and/or contact detection signal; a second capacitive sensor including a second electrode, detecting the approach of a human body part in the predetermined region, wherein: the first and second electrodes are each separate segments electrically connected to one another, the segments of the first electrode and of the second electrode are alternately juxtaposed; a second sensor controller generate a second approach and/or contact detection signal; a correlator to calculate a correlation value between the first signal and the
(Continued)

second signal; and a confirmation unit comparing the correlation value with a predetermined value to detect intention to lock or unlock the door.

20 Claims, 3 Drawing Sheets

(51) Int. Cl.
| | |
|---|---|
| *E05B 81/78* | (2014.01) |
| *G01N 27/22* | (2006.01) |
| *G01N 33/28* | (2006.01) |
| *G01R 27/02* | (2006.01) |
| *G01R 27/26* | (2006.01) |
| *G01V 3/38* | (2006.01) |

(52) U.S. Cl.
CPC ..... *G01R 27/2605* (2013.01); *G01R 27/2635* (2013.01); *G01V 3/38* (2013.01); *G01N 27/221* (2013.01); *G01N 27/223* (2013.01); *G01N 33/2852* (2013.01)

(58) Field of Classification Search
CPC ............ G07C 2209/65; G07C 9/00309; H03K 17/955; H03K 17/9622; G01R 27/2605; G01R 27/2635; G01R 27/02; G01N 27/223; G01N 27/221; G01N 33/2852
USPC ......................................................... 324/672
See application file for complete search history.

(56) References Cited

U.S. PATENT DOCUMENTS

| | | |
|---|---|---|
| 8,542,208 B2 | 9/2013 | Krah et al. |
| 8,823,660 B2 | 9/2014 | Krah et al. |
| 8,970,288 B2 | 3/2015 | Hourne et al. |
| 9,383,843 B2 | 7/2016 | Krah et al. |
| 10,712,866 B2 | 7/2020 | Krah et al. |
| 11,194,423 B2 | 12/2021 | Krah et al. |
| 2006/0042638 A1 | 3/2006 | Niklewski et al. |
| 2013/0033362 A1* | 2/2013 | Hourne .................. E05B 81/77 340/5.72 |
| 2017/0194960 A1* | 7/2017 | Bextermoeller ........ E05B 81/77 |
| 2017/0235008 A1 | 8/2017 | Guibbert et al. |
| 2019/0368238 A1* | 12/2019 | Spick ................... H03K 17/954 |
| 2019/0390487 A1* | 12/2019 | Spick ...................... E05B 83/36 |
| 2021/0072046 A1* | 3/2021 | Van Gastel .......... H03K 17/955 |
| 2021/0123270 A1* | 4/2021 | Spick ..................... E05B 81/76 |

FOREIGN PATENT DOCUMENTS

| | | |
|---|---|---|
| CN | 101778982 A | 7/2010 |
| CN | 202798643 U | 3/2013 |
| CN | 104081666 A | 10/2014 |
| CN | 104237949 A | 12/2014 |
| CN | 106484191 A | 3/2017 |
| CN | 106778508 A | 5/2017 |
| CN | 107083883 A | 8/2017 |
| CN | 107554080 A | 1/2018 |
| DE | 10 2007 021 812 A1 | 11/2008 |
| DE | 10 2016 217 545 | 3/2018 |
| JP | 2018-3468 A | 1/2018 |
| WO | 2012/107415 | 8/2012 |
| WO | 2013/079642 | 6/2013 |
| WO | 2018/091829 | 5/2018 |

OTHER PUBLICATIONS

Office Action issued in Chinese Patent Application No. 201980068530.0 dated Jun. 24, 2022.
International Search Report for PCT/EP2019/077859 dated Dec. 9, 2019, 7 pages.
Written Opinion of the ISA for PCT/EP2019/077859 dated Dec. 9, 2019, 8 pages.

* cited by examiner

DEVICE FOR DETECTING INTENTION TO LOCK OR UNLOCK A MOTOR VEHICLE DOOR AND ASSOCIATED METHOD

CROSS-REFERENCE TO RELATED APPLICATIONS

This application is the U.S. national phase of International Application No. PCT/EP2019/077859 filed Oct. 15, 2019 which designated the U.S. and claims priority to FR 1859691 filed Oct. 19, 2018, the entire contents of each of which are hereby incorporated by reference.

BACKGROUND OF THE INVENTION

Field of the Invention

The invention relates to a device for detecting a user's intention to lock or unlock a motor vehicle door, to an associated detection method and to a vehicle door handle comprising said device.

Description of the Related Art

Nowadays, vehicle door handles are equipped with devices for detecting intention to lock or unlock a door. Said detection, coupled with the recognition of a "hands-free" electronic remote access control fob, carried by this user, allows the opening elements of the vehicle to be locked and unlocked remotely. Thus, when the user, carrying the corresponding electronic fob identified by the vehicle, wishes to unlock the vehicle, he touches the door handle of the vehicle and the opening elements of the vehicle are then unlocked automatically. By approaching or by pressing on a precise location of the door handle of the vehicle, called "unlocking region", the door (or alternatively all of the opening elements) is (are) unlocked without any other action from the user. Conversely, when the user, still carrying the necessary fob identified by the vehicle, wishes to lock his vehicle, he closes the door of his vehicle and he presses momentarily on another precise location of the handle, called "locking region". This movement makes it possible to lock the opening elements of the vehicle automatically.

These presence detection devices generally comprise two capacitive sensors, in the form of two electrodes connected electrically to a printed circuit board and integrated into the door handle, each in a precise locking or unlocking region. Generally, one electrode is dedicated to each region, that is to say one electrode is dedicated to detecting the approach and/or contact of the hand of the user in the locking region and one electrode is dedicated to detecting the approach and/or contact of the hand of the user in the unlocking region.

The presence detection device furthermore comprises a generally LF (abbreviation for "low-frequency") radiofrequency antenna. The detection device is connected to the electronic computer of the vehicle (ECU: abbreviation for "electronic control unit") and sends it a presence detection signal. The electronic computer of the vehicle has, beforehand, identified the user as being authorized to access this vehicle, or alternatively, following the reception of this presence detection signal, it performs this identification. To this end, it sends an identification request to the fob (or to the remote controller) carried by the user by way of the radiofrequency antenna. This fob in response sends its identification code to the electronic computer of the vehicle through RF (radiofrequency) waves. If the electronic computer recognizes the identification code as the one authorizing access to the vehicle, it triggers the locking/unlocking of the door (or of all of the opening elements). If, on the other hand, the electronic computer has not received any identification code or if the received identification code is erroneous, locking or unlocking is not performed.

Such vehicles are therefore equipped with door handles comprising a detection device, itself comprising a generally low-frequency radiofrequency antenna, and two electrodes connected to a microcontroller, integrated into a printed circuit board and supplied with a voltage.

Purely for the sake of explanation, consideration will be given here to a detection device D comprising two capacitive sensors in the form of two electrodes, one electrode dedicated to the unlocking region and one electrode dedicated to the locking region, said two electrodes being connected to a printed circuit board comprising a microcontroller, and an LF antenna. A detection device D from the prior art is described with reference to FIG. 1.

FIG. 1 shows a motor vehicle door P handle 10 (vehicle not shown) in which there is located a device D for detecting the presence of a user. Said door P handle 10 comprises a first outer surface S1 oriented in the direction of the door P and a second outer surface S2, opposite the first outer surface S1 and therefore oriented on the side opposite the vehicle, more precisely toward the user (not shown). This detection device D, which generally takes the form of a watertight housing B, comprises a first unlocking electrode E2, one face of which is located close to the first outer surface S1, an LF antenna (not shown), one face of which is located close to the second outer surface S2, a second locking electrode E1, one face of which is located close to the second outer surface S2, and control means 60. The first and the second electrode E1, E2 are connected to the control means 60. These control means 60 measure the capacitance between the terminal of each first and second electrode E1, E2 and ground, formed by the hand of the approaching user, so as to detect the presence (the approach and/or contact) of a user in the detection regions, that is to say in a locking region Z1 or in an unlocking region Z2, and consist for example of a microcontroller 60 integrated into a printed circuit board 80. The LF antenna (not shown) is for its part connected to an electronic computer on board the vehicle (not shown) of BCM ("body controller module") type, which manages the identification requests transmitted by said LF antenna. When the hand M of the user approaches the electrode E1 or E2, the user acts as a second electrode, connected to ground, which increases the capacitance value of the detection capacitor to a capacitance value higher than the nominal capacitance value of the detection capacitor "at rest" (i.e. in the absence of a user).

The change in the capacitance value above a threshold confirms detection of the approach of the hand of the user.

However, this detection device D from the prior art exhibits major drawbacks.

Specifically, detection of the approach of a user using capacitive sensors (first and second electrode E1 and E2) is not robust and generates false detections.

In particular, in some environmental conditions, when raindrops or snowflakes come into contact with the door handle, these increase the capacitance value measured by the capacitive sensors, thus triggering false detections.

SUMMARY OF THE INVENTION

The invention therefore proposes a method and a device for detecting a user's intention to lock or unlock the door of a vehicle, making it possible to reduce the number of false detections due to rain or to snowflakes.

The invention proposes a device for detecting intention to lock or unlock a door of a vehicle, said device comprising at least:
- a first capacitive sensor comprising a first electrode, capable of detecting the approach and/or contact of a human body part in a predetermined region around the handle,
- control means for controlling said first sensor, generating a first approach and/or contact detection signal,
  said device being noteworthy in that it furthermore comprises:
- a second capacitive sensor comprising a second electrode, capable of detecting the approach and/or contact of a human body part in the predetermined region around the handle, such that:
- the first electrode and the second electrode are each in the form of separate segments that are electrically connected to one another, said segments of the first electrode and the second electrode being alternately juxtaposed,
- control means for controlling said second sensor, generating a second approach and/or contact detection signal,
- correlation means calculating a correlation value between the first signal and the second signal,
- confirmation means comparing said correlation value with a predetermined value in order to detect intention to lock or unlock the door.

Advantageously, said segments are positioned and dimensioned such that the approach and/or contact of a part of a body of a user is detected on at least two juxtaposed segments each belonging to a different electrode.

In one preferred embodiment, the segments are in the form of rectangles.

Said segments are expediently identical in size and identical in number for each electrode.

In the preferred embodiment, with the segments being in the form of rectangles of predetermined length and width, said segments are juxtaposed over their length.

The correlation value may consist of a period between a first time corresponding to the first signal exceeding a predetermined first threshold and a second time corresponding to the second signal exceeding a predetermined second threshold.

In the preferred embodiment, the predetermined first threshold and the predetermined second threshold have equal values.

The invention also relates to a method for detecting intention to lock or unlock a door of a vehicle, using a detection device comprising at least one first capacitive sensor comprising a first electrode, capable of detecting the approach and/or contact of a human body part in a predetermined region around the handle, and control means for controlling said first sensor, generating a first approach and/or contact detection signal, said method being noteworthy in that it comprises the following steps:
- in a preliminary step, the device is fitted with a second capacitive sensor comprising a second electrode, capable of detecting the approach of a human body part in the predetermined region around the handle, such that:
  the first electrode and the second electrode are each in the form of separate segments that are electrically connected to one another,
  said segments of the first electrode and of the second electrode are alternately juxtaposed,
  and control means for controlling said second sensor, generating a second approach and/or contact detection signal,
- it is determined whether there is a correlation between the first signal and the second signal: if there is a correlation, then there is confirmation of detection of intention to lock or unlock; if not, there is no detection confirmation.

In one embodiment of the method according to the invention, the correlation exists if a period between a first time corresponding to the first signal exceeding a predetermined first threshold and a second time corresponding to the second signal exceeding a predetermined second threshold is less than a predetermined duration.

The invention is also applicable to any motor vehicle door handle comprising a detection device according to any one of the features listed above.

Finally, the invention is also applicable to any motor vehicle comprising a detection device according to any one of the features listed above.

BRIEF DESCRIPTION OF THE DRAWINGS

Other aims, features and advantages of the invention will become apparent upon reading the following description provided by way of non-limiting example and upon examining the appended drawings, in which.

DESCRIPTION OF THE PREFERRED EMBODIMENTS

Figure 4:
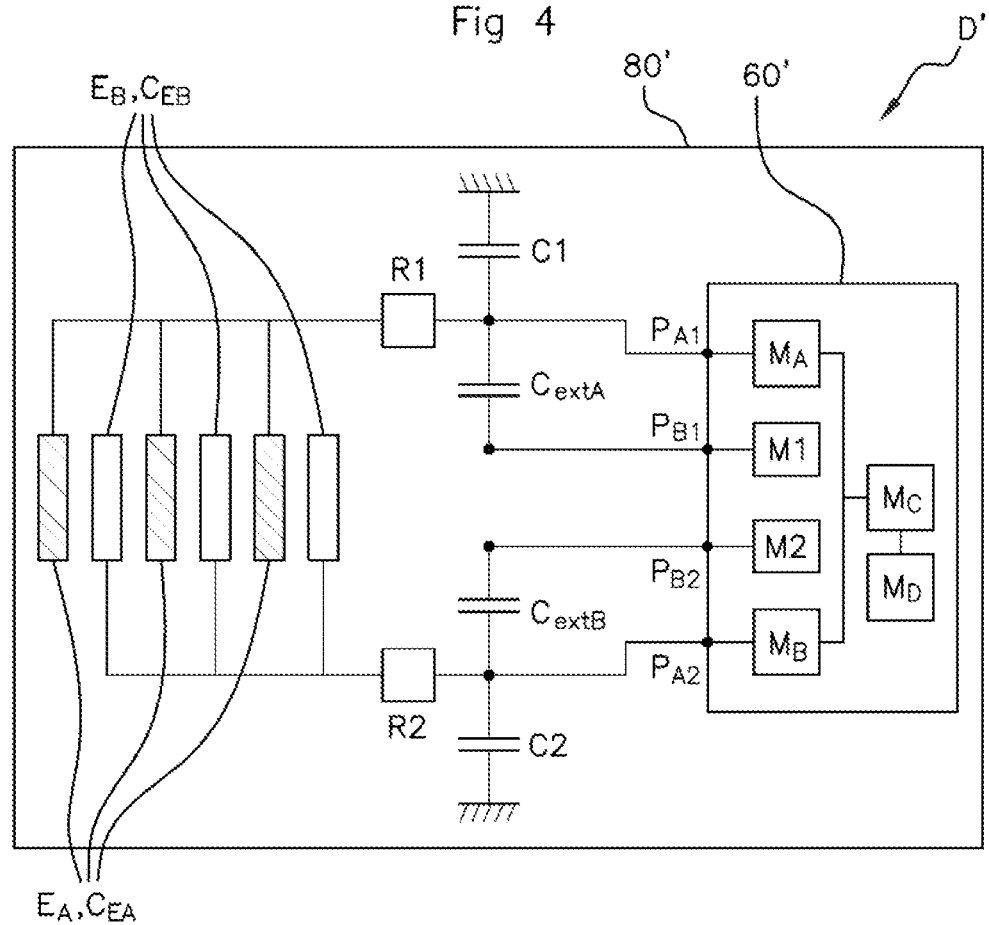
Figure 5:
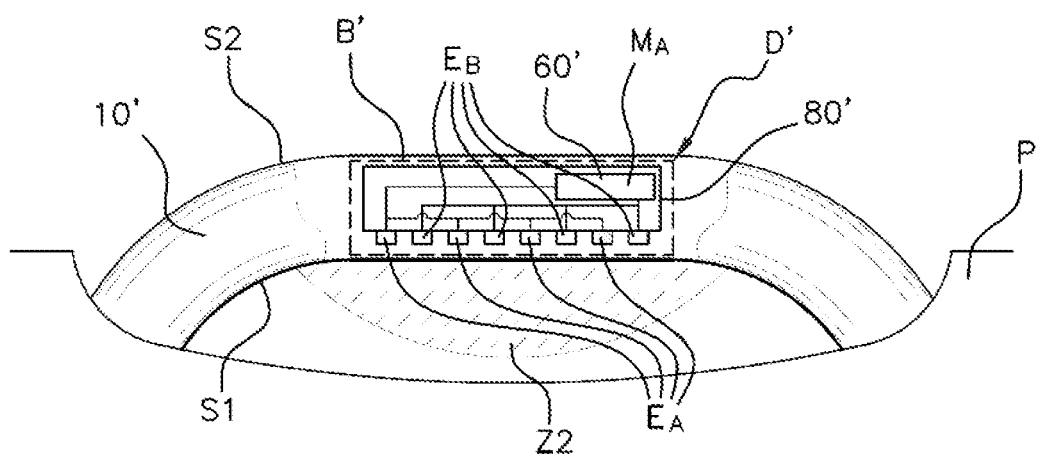

The device D' for detecting intention to lock or unlock a door P of a motor vehicle according to the invention is illustrated in FIGS. 4 and 5.

The detection device D' is contained in a door P handle 10'.

Purely for the sake of explanation, the invention will be explained for a device for detecting intention to unlock the door P. More precisely, this relates to a device designed to detect the approach of a hand of a user in an unlocking region Z2 located between the handle 10' and the door P (cf. FIG. 5). Of course, the invention also applies similarly to a device for detecting intention to lock the door P.

As illustrated in FIG. 5, the device D' for detecting intention to unlock a door P of a vehicle comprises:

a first capacitive sensor comprising a first electrode $E_A$, capable of detecting the approach and/or contact of a human body part in the predetermined region Z2 around the handle 10', control means $M_A$ for controlling said first sensor, generating a first approach and/or contact detection signal $N_A$.

The first capacitive sensor comprises a first electrode $E_A$ of capacitance $C_{EA}$, connected to control means $M_A$ for controlling said sensor that are located for example in a microcontroller 60' that is itself integrated into a printed circuit board 80'.

As illustrated in FIG. 4, the control means $M_A$ are connected to the first electrode $E_A$ by way of a CVD or "capacitive voltage divider" measuring circuit comprising a first resistor R1, a first capacitor C1 and a measuring capacitor $C_{extA}$. The first electrode $E_A$ is connected to the first resistor R1, which is itself connected via a first branch to the first capacitor C1 that is connected to ground, via a second branch to the control means $M_A$ located in the microcontroller 60', and via a third branch to the measuring capacitor $C_{etxA}$ connected to an input/output controller M1 or GPIO ("general purpose input/output") controller also located in the microcontroller 60'. The control means $M_A$ comprise an input/output controller and an ADC ("analog to digital converter") that are not shown in FIG. 4.

The operation of the CVD circuit, the circuit for measuring the capacitance $C_{EA}$ of the first electrode $E_A$, thus formed is as follows:

The measuring capacitor $C_{extA}$ is first of all discharged. Then, using the input/output controller M1 and control means $M_A$ that are positioned at output, the first capacitor C1 as well as the capacitance of the first electrode $C_{EA}$ are charged until charging is complete. Then, using the control means $M_A$ positioned at input, the first capacitor C1 and the capacitance of the first electrode $C_{EA}$ are discharged into measuring capacitor $C_{extA}$ until discharging is complete. The voltage across the terminals of the measuring capacitor $C_{extA}$ is then measured using the control means $M_A$. Said voltage across the terminals of the measuring capacitor $C_{extA}$ is proportional to the value of the capacitance $C_{EA}$ of the first electrode $E_A$, which increases as a part of the human body approaches toward said first electrode $E_A$.

The control means $M_A$ then generate a first detection signal $N_A$, representative of the value of the capacitance $C_{EA}$, which increases with the approach and/or contact of a part of the body of the user toward or with the first electrode $E_A$.

The capacitive detection method, in this case using the capacitive voltage divider, is known to a person skilled in the art and will not be described in more detail here.

Of course, other capacitive detection devices and methods are possible, the capacitive voltage divider being given only by way of example.

According to the invention, the detection device D' comprises a second capacitive sensor itself comprising a second electrode $E_B$ having a capacitance $C_{EB}$. Said second capacitive sensor, like the first capacitive sensor, is capable of detecting the approach and/or contact of a part of the human body close to the same unlocking region Z2.

The second electrode $E_B$ of the second capacitive sensor is connected to control means $M_B$ for controlling said sensor, similarly via a CVD circuit, or a capacitive voltage divider circuit, comprising a second resistor R2 and a second capacitor C2 and a measuring capacitor $C_{extB}$.

The second control means $M_B$ are for example located in the microcontroller 60', integrated into the printed circuit board 80' and comprise an input/output controller and an ADC ("analog to digital converter").

The second electrode $E_B$ is connected to the second resistor R2, which is itself connected via a first branch to the second capacitor C2 and to ground, via a second branch to the control means $M_B$, and via a third branch to the measuring capacitor $C_{extB}$ connected to an input/output controller M2 or GPIO ("general purpose input/output") controller also located in the microcontroller 60'.

Similarly, the CVD circuit, that is to say the circuit for measuring the capacitance $C_{EB}$ of the second electrode $E_B$ thus formed, operates as follows:

The measuring capacitor $C_{extB}$ is first of all discharged. Then, using the input/output controller M2 and control means $M_B$ that are positioned at output, the second capacitor C2 as well as the capacitance of the second electrode $C_{EB}$ are charged until charging is complete. Then, using the control means $M_B$ positioned at input, the second capacitor C2 and the capacitance of the second electrode $C_{EB}$ are discharged into measuring capacitor $C_{extB}$ until discharging is complete. The voltage across the terminals of the measuring capacitor $C_{extB}$ is then measured using the control means $M_B$. Said voltage across the terminals of the measuring capacitor $C_{extB}$ is proportional to the value of the capacitance $C_{EB}$ of the second electrode $E_B$, which increases as a part of the human body approaches toward said second electrode $E_B$.

The control means $M_B$ then generate a second detection signal $N_B$, representative of the value of the capacitance $C_{EB}$, which increases with the approach and/or contact of a part of the body of the user toward or with the second electrode $E_B$.

According to the invention, and in contrast to the prior art, not only does the detection device D' therefore comprise two capacitive sensors dedicated to detecting approach and/or contact toward or with the same predetermined region around the handle 10', in this example the unlocking region Z2, but the invention also proposes for the first electrode $E_A$ and the second electrode $E_B$ to each be in the form of separate segments that are electrically connected to one another, and for said segments of the first electrode $E_A$ and the second electrode $E_B$ to be alternately juxtaposed.

Figure 1:
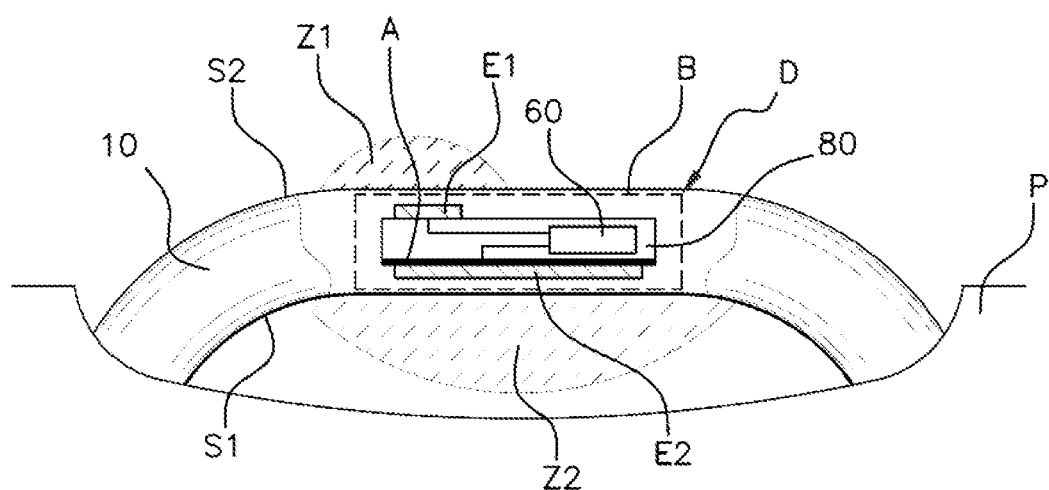
FIG. 1 schematically shows the detection device D from the prior art, integrated into a motor vehicle door P handle 10, FIG. 2 schematically shows an assembly of two electrodes associated with a single detection region, contained in a detection device D' according to the invention, FIG. 3 comprises two graphs.
Figure 2:
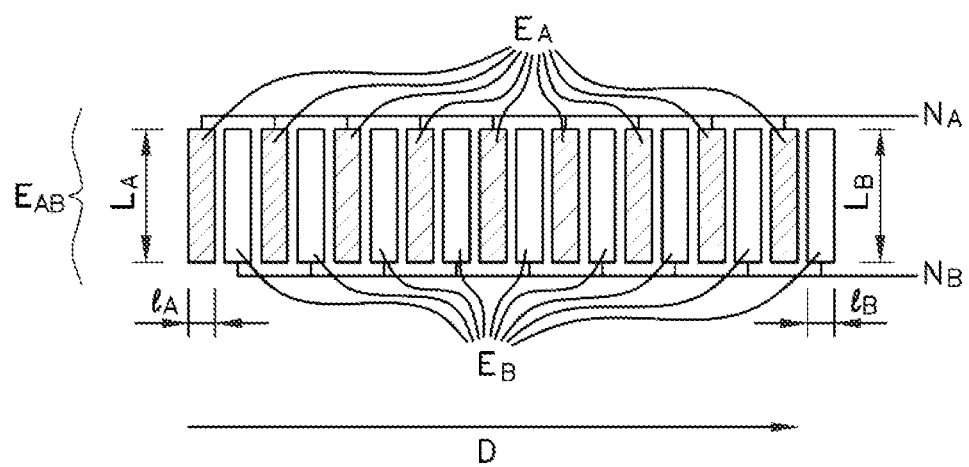

One preferred embodiment of the first and second electrodes $E_A$, $E_B$ according to the invention is illustrated in FIG. 2.

The first electrode $E_A$ comprises a plurality of separate segments, that is to say not juxtaposed with one another, but that are electrically connected to one another so as to form a single first electrode $E_A$.

Similarly, the second electrode $E_B$ comprises a plurality of separate segments, that is to say not juxtaposed with one another, but that are electrically connected to one another so as to form a single second electrode $E_B$.

According to the invention, the segments of the first electrode $E_A$ and the segments of the second electrode $E_B$ are arranged in a specific way, in this case at least one segment of the second electrode $E_B$ is located next to each segment of the first electrode $E_A$, and vice versa.

The segments of the first electrode $E_A$ and of the second electrode $E_B$ are alternately placed side by side in for example a predetermined direction D that corresponds to a dimension of the detection region, here of the unlocking region Z2; this is the length of said region in this example. A segment of the first electrode $E_A$ is juxtaposed next to a segment of the second electrode $E_B$, which is itself juxtaposed next to a segment of the first electrode $E_A$.

Segment is understood to mean any parallelepipedal shape, polygonal shape or geometric shape with curved or rounded edges, such as a portion of a disk, a half disk, a solid triangle, a solid square, a rectangle, etc., such that it is possible to juxtapose two segments next to one another.

Juxtapose is understood to mean the fact that the segments are arranged such that the space or the distance between two successive segments is as small as possible; this is explained below.

According to the invention, the detection device D' comprises correlation means $M_C$ for correlating the first signal $N_A$ and the second signal $N_B$.

The correlation means $M_C$ are for example in the form of software, contained in the microcontroller 60'.

Figure 3:
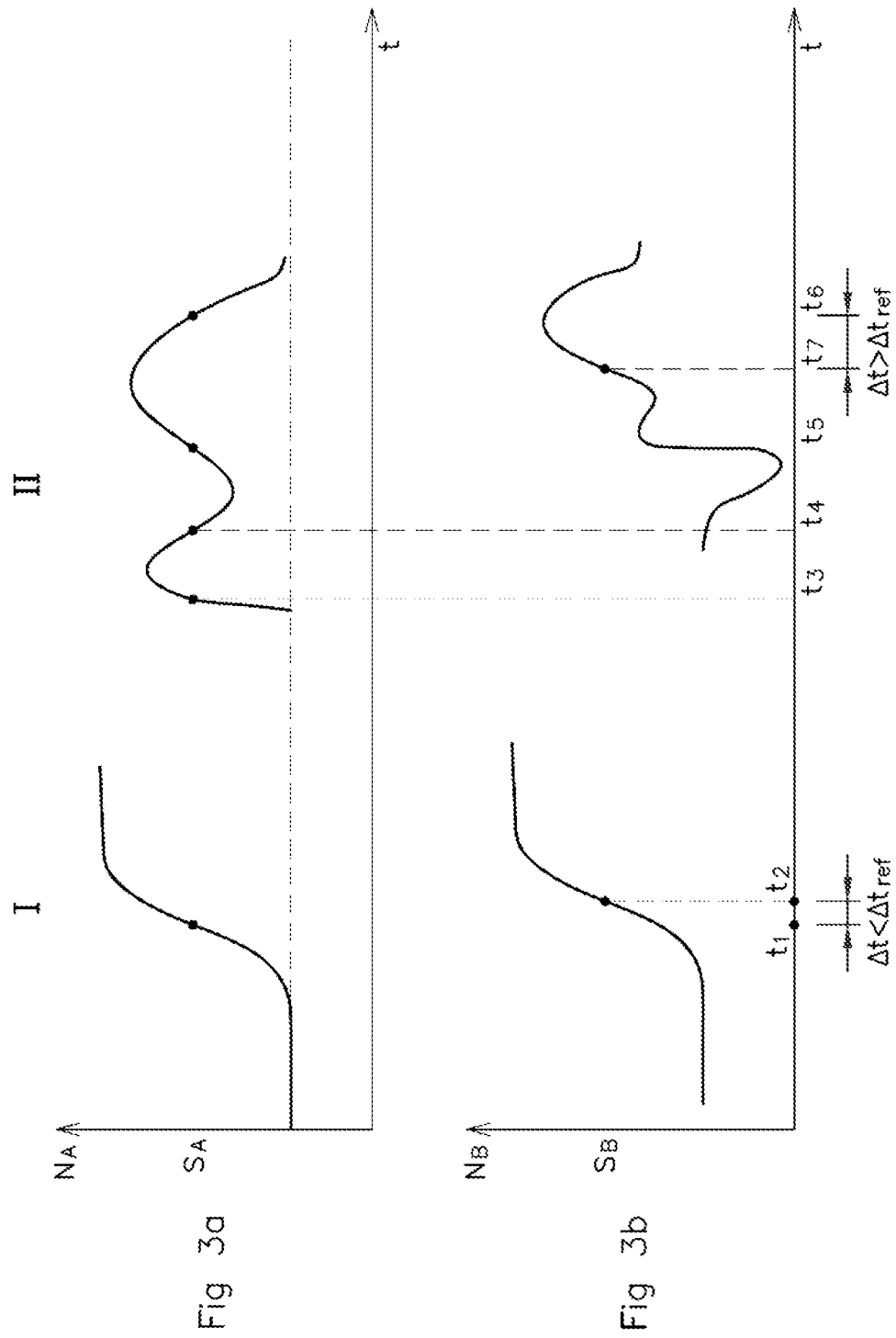
FIG. 3a shows, as a function of time t, the variation in capacitance $N_A$ of the first electrode of the electrode assembly of the detection device according to the invention, illustrated in FIG. 2.
FIG. 3b shows, as a function of time t, the variation in capacitance $N_B$ of the second electrode of the electrode assembly of the detection device according to the invention, illustrated in FIG. 2, specifically for two cases, case I, where detection is confirmed, case II, where detection is not confirmed, FIG. 4 schematically shows the detection device D' according to the invention, FIG. 5 schematically shows the detection device D of the invention, integrated into a motor vehicle door P handle 10'.

The correlation means $M_C$ consist for example of means for calculating a period $\Delta t$ between a first time t1 corresponding to the first signal $N_A$ exceeding a predetermined first threshold $S_A$ and a second time t2 corresponding to the second signal $N_B$ exceeding a predetermined second threshold $S_B$ (cf. FIG. 3). Detection means $M_D$ compare $\Delta t$, said period thus calculated, with a predetermined duration $\Delta t_{ref}$ in order to confirm or not confirm detection.

The correlation means $M_C$ may of course consist of any mathematical formula that makes it possible to determine whether the first signal $N_A$ and whether the second signal $N_B$ have a similar shape and a similar amplitude, to within a factor. The factor may be for example a multiplication or addition factor on the amplitude and/or a time shift factor on the shape. The result of applying the mathematical formula is a correlation coefficient that is then compared with a predetermined correlation coefficient by detection means $M_D$.

Depending on the correlation result compared with predetermined values, the detection means $M_D$ confirm or do not confirm approach and/or contact detection.

A person skilled in the art knows how to compare two signals with one another in order to determine whether or not they are correlated.

Of course, the correlation result is compared with a predetermined value, which makes it possible to confirm the correlation.

In one preferred embodiment of the invention, said segments are in the form of rectangles of conductive metal, for example copper, positioned and dimensioned such that the approach and/or contact of a part of a body of a user is detected on at least two juxtaposed segments each belonging to a different electrode, that is to say on at least one segment of the first electrode $E_A$ and on at least one segment of the second electrode $E_B$.

It is important to note that the dimensions of the segments should be adapted so that each segment is able to detect at least one drop of water, but the dimensions should above all be smaller than the average size of a finger. The dimensions of the surface area of a segment should not be smaller than the dimensions of a drop of water or of a snowflake.

Specifically, the reasoning underlying the invention is that, with the segments dimensioned in this way, a finger is detected almost simultaneously by two juxtaposed (or successive) segments and therefore by the two electrodes, and conversely, the probability of two drops of water touching the two segments almost simultaneously, and therefore of a raindrop being detected almost simultaneously by the two electrodes $E_A$, $E_B$, is very low.

The detection device D', with an arrangement of electrodes $E_A$, $E_B$ as described above, therefore makes it possible to distinguish between the approach and/or contact of a part of the body of the user in the locking region Z2 and contact between a raindrop and said region.

In the preferred embodiment of the detection device D' illustrated in FIG. 2, the segments are in the form of rectangles, of length $L_A$ and of width $l_a$ for the segments of the first electrode $E_A$ and of length $L_B$ and of width $l_b$ for the segments of the second electrode $E_B$, such that the segments are identical in size, that is to say $L_A=L_B$ and $l_a=l_b$, and identical in number for each electrode.

There are thus as many segments of the first electrode $E_A$ as there are segments of the second electrode $E_B$.

Plus, with the segments being in the form of rectangles of predetermined length and width $L_A, L_B, l_A, l_B$, said segments are juxtaposed over their length.

Thus, in this preferred embodiment, with the sensitive copper surfaces of the two electrodes $E_A$, $E_B$ being of the same dimensions, and the number of segments being identical for the two electrodes $E_A$, $E_B$, the two electrodes therefore have the same detection sensitivity.

In this preferred embodiment, the predetermined first threshold $S_A$ and the predetermined second threshold $S_3$ are of equal value.

The detection method according to the invention will now be described.

In a preliminary step, the detection device D' is additionally fitted with a first capacitive sensor comprising the first electrode $E_A$ and the control means $M_A$, with a second capacitive sensor comprising a second electrode $E_B$ and with control means $M_3$ for controlling said second sensor, in accordance with the features listed above.

Then, in a secondary step, it is determined whether there is a correlation between the first signal $N_A$ from the first electrode $E_A$ and the second signal $N_B$ from the second electrode $E_B$. If there is a correlation, or if the result of the correlation is greater than a predetermined value, then there is confirmation of detection of intention to lock or unlock; if not, there is no confirmation.

This is illustrated in FIG. 3. FIG. 3a shows the first signal $N_A$ as a function of time t, and FIG. 3b shows the second signal $N_B$ as a function of time t, in the case of the preferred embodiment of the detection device D' according to the invention, specifically the first electrode $E_A$ and the second electrode $E_B$ have a sensitivity substantially equal to one another.

Each signal is shown for two cases;
case I: detection of intention to unlock is confirmed,
case II: detection of intention to unlock is not confirmed.

For case I, the user brings his hand into the unlocking region Z2, such that part of his hand is detected by the first electrode $E_A$ and by the second electrode $E_B$ almost simultaneously.

The first signal $N_A$, when the hand of the user approaches toward the handle 10', in the unlocking region Z2 increases until it crosses a first threshold $S_A$ at the first time t1.

Similarly, the second signal $N_B$, when the hand of the user approaches toward the handle 10', in the unlocking region Z2 increases until it crosses a second threshold $S_B$ at the second time t2.

In the example illustrated in FIG. 3, the correlation between the two signals is established by calculating a period $\Delta t$ between the second time t2 and the first time t1.

If said period $\Delta t$ is less than a predetermined duration $\Delta t_{ref}$, then it is considered that there is a correlation between the first signal $N_A$ and the second signal $N_B$, and therefore detection of intention to unlock is confirmed.

For case II, the first signal $N_A$ crosses the first threshold $S_A$ at four successive times; third time t3, fourth time t4, fifth time t5, sixth time t6. The second signal $N_B$ for its part crosses the second threshold $S_B$ at just one time, a seventh time t7.

If the period between one of the times of crossing of the first signal $N_A$, for example t6 (or t3, or t4, or t5), and the time of crossing of the second signal $N_B$, that is to say the seventh time t7, i.e. Δt', is calculated, it appears that said period thus calculated is greater than the predetermined duration $\Delta t_{ref}$.

There is therefore no correlation between the first signal $N_A$ and the second signal $N_B$, and detection of intention to unlock is therefore not confirmed.

The invention therefore expediently makes it possible to considerably reduce false detections caused by the impact of raindrops in the unlocking region.

The invention therefore allows reliable and robust detection of intention to lock or unlock the door of a motor vehicle.

The invention claimed is:

1. A device (D') for detecting intention to lock or unlock a door (P) of a vehicle, said device (D') comprising at least:
   a first capacitive sensor comprising a first electrode ($E_A$), capable of detecting the approach and/or contact of a human body part in a predetermined region (Z2) around the handle (10');
   a second capacitive sensor comprising a second electrode ($E_B$), capable of detecting the approach and/or contact of a human body part in the predetermined region (Z2) around the handle (10'); and
   a microcontroller (60'),
   wherein the first electrode ($E_A$) and the second electrode ($E_B$) are each formed as separate segments that are electrically connected to one another, and said segments of the first electrode ($E_A$) and of the second electrode ($E_B$) being alternately juxtaposed, and
   wherein the microcontroller (60') is configured to operate as:
      control means ($M_A$) that controls said first capacitive sensor and generates a first approach and/or contact detection signal (NA),
      control means ($M_B$) that controls said second capacitive sensor and generates a second approach and/or contact detection signal ($N_B$),
      correlation means ($M_C$) that calculates a correlation value between the first approach and/or contact detection signal ($N_A$) and the second approach and/or contact detection signal ($N_B$), and
      confirmation means ($M_D$) that compares said correlation value with a predetermined value in order to detect intention to lock or unlock the door (10').

2. The detection device (D') as claimed in claim 1, wherein said segments are positioned and dimensioned such that the approach and/or contact of a part of a body of a user is detected on at least two juxtaposed segments each belonging to a different electrode.

3. The detection device (D') as claimed in claim 2, wherein the segments are in the form of rectangles.

4. The detection device (D') as claimed in claim 1, wherein said segments are identical in size and identical in number for each electrode.

5. The detection device (D') as claimed in claim 4, wherein the segments are in the form of rectangles of predetermined length and width, and said segments are juxtaposed over their length.

6. The detection device (D') as claimed in claim 1, wherein the correlation value consists of a period (Δt) between a first time (t1) corresponding to the first approach and/or contact detection signal ($N_A$) exceeding a predetermined first threshold ($S_A$) and a second time (t2) corresponding to the second approach and/or contact detection signal ($N_B$) exceeding a predetermined second threshold ($S_B$).

7. The detection device (D') as claimed in claim 6, wherein the predetermined first threshold ($S_A$) and the predetermined second threshold ($S_B$) are of equal values.

8. A motor vehicle door handle (10'), comprising the detection device (D') as claimed in claim 1.

9. A motor vehicle, comprising the detection device (D') as claimed in claim 1.

10. The detection device (D') as claimed in claim 2 said segments are identical in size and identical in number for each electrode.

11. The detection device (D') as claimed in claim 2, wherein the correlation value consists of a period (Δt) between a first time (t1) corresponding to the first approach and/or contact detection signal ($N_A$) exceeding a predetermined first threshold ($S_A$) and a second time (t2) corresponding to the second approach and/or contact detection signal ($N_B$) exceeding a predetermined second threshold ($S_B$).

12. The detection device (D') as claimed in claim 3, wherein the correlation value consists of a period (Δt) between a first time (t1) corresponding to the first approach and/or contact detection signal ($N_A$) exceeding a predetermined first threshold ($S_A$) and a second time (t2) corresponding to the second approach and/or contact detection signal ($N_B$) exceeding a predetermined second threshold ($S_B$).

13. The detection device (D') as claimed in claim 4, wherein the correlation value consists of a period (Δt) between a first time (t1) corresponding to the first approach and/or contact detection signal ($N_A$) exceeding a predetermined first threshold ($S_A$) and a second time (t2) corresponding to the second approach and/or contact detection signal ($N_B$) exceeding a predetermined second threshold ($S_B$).

14. The detection device (D') as claimed in claim 5, wherein the correlation value consists of a period (Δt) between a first time (t1) corresponding to the first approach and/or contact detection signal ($N_A$) exceeding a predetermined first threshold ($S_A$) and a second time (t2) corresponding to the second approach and/or contact detection signal ($N_B$) exceeding a predetermined second threshold ($S_B$).

15. A motor vehicle door handle (10'), comprising the detection device (D') as claimed in claim 2.

16. A motor vehicle door handle (10'), comprising the detection device (D') as claimed in claim 3.

17. A motor vehicle door handle (10'), comprising the detection device (D') as claimed in claim 4.

18. A motor vehicle door handle (10'), comprising the detection device (D') as claimed in claim 5.

19. A method for detecting intention to lock or unlock a door (P) of a vehicle, said method comprising the following steps:
   providing a detection device (D') that includes
      a first capacitive sensor with a first electrode ($E_A$), capable of detecting the approach and/or contact of a human body part in a predetermined region (Z2) around the handle (10'),
      a second capacitive sensor with a second electrode ($E_B$), capable of detecting the approach and/or contact of a human body part in the predetermined region (Z2) around the handle (10'), and
      a microcontroller (60'),
      the first electrode ($E_A$) and the second electrode ($E_B$) each formed as separate segments that are electrically connected to one another, and said segments of the first electrode ($E_A$) and of the second electrode ($E_B$) being alternately juxtaposed, and the microcontroller (60') being configured to operate as:

control means ($M_A$) that controls said first capacitive sensor and generates a first approach and/or contact detection signal ($S_A$), and control means ($M_B$) that controls said second capacitive sensor and generates a second approach and/or contact detection signal ($N_B$);

and determining, via the microcontroller, whether there is a correlation between the first approach and/or contact detection signal ($N_A$) and the second approach and/or contact detection signal ($N_B$), such that:

if there is a correlation, then there is confirmation of detection of intention to lock or unlock; and if not, there is no confirmation.

20. The detection method as claimed in claim 19, wherein the correlation exists if a period ($\Delta t$) between a first time (t1) corresponding to the first approach and/or contact detection signal ($N_A$) exceeding a predetermined first threshold ($S_A$) and a second time (t2) corresponding to the second approach and/or contact detection signal ($N_B$) exceeding a predetermined second threshold ($S_B$) is less than a predetermined duration ($\Delta t_{ref}$).

* * * * *